(12) United States Patent
Blacker

(10) Patent No.: US 9,789,285 B1
(45) Date of Patent: Oct. 17, 2017

(54) WIPING MECHANISM FOR A Y-CONNECTOR

(71) Applicant: Corindus, Inc., Waltham, MA (US)

(72) Inventor: Steven J. Blacker, Framingham, MA (US)

(73) Assignee: CORINDUS, INC., Waltham, MA (US)

( * ) Notice: Subject to any disclaimer, the term of this patent is extended or adjusted under 35 U.S.C. 154(b) by 422 days.

(21) Appl. No.: 14/216,076

(22) Filed: Mar. 17, 2014

Related U.S. Application Data

(60) Provisional application No. 61/792,353, filed on Mar. 15, 2013.

(51) Int. Cl.
- *A61M 25/01* (2006.01)
- *A61M 39/06* (2006.01)
- *A61B 19/00* (2006.01)

(52) U.S. Cl.
CPC ......... *A61M 25/0116* (2013.01); *A61B 19/34* (2013.01); *A61M 39/06* (2013.01); *A61M 2039/062* (2013.01); *A61M 2210/12* (2013.01)

(58) Field of Classification Search
CPC .......... A61M 25/0105; A61M 25/0113; A61M 25/0116; A61M 39/06; A61B 34/00; A61B 34/30; A61B 34/32; A61B 34/35; A61B 34/37; A61B 34/70; A61B 34/71; A61B 2034/301; A61B 2034/302; A61B 2034/303; A61B 2034/304; A61B 2034/305; A61B 2034/306

USPC ......... 604/95.01, 95.02, 95.03, 95.04, 95.05, 604/528; 606/130

See application file for complete search history.

(56) References Cited

U.S. PATENT DOCUMENTS

| | | | | |
|---|---|---|---|---|
| 3,721,252 A | * | 3/1973 | Ayella | E03C 1/046 134/122 R |
| 2002/0111585 A1 | * | 8/2002 | Lafontaine | A61M 39/0606 604/167.06 |
| 2007/0260115 A1 | * | 11/2007 | Brock | A61B 90/36 600/114 |
| 2009/0322543 A1 | * | 12/2009 | Crnkovich | A61F 13/42 340/604 |
| 2011/0087224 A1 | * | 4/2011 | Cadeddu | A61B 18/14 606/49 |
| 2011/0313415 A1 | * | 12/2011 | Fernandez | A61B 5/062 606/41 |
| 2012/0197200 A1 | * | 8/2012 | Belson | A61M 25/0606 604/164.12 |
| 2014/0066899 A1 | | 3/2014 | Blacker | |
| 2014/0066900 A1 | | 3/2014 | Blacker | |
| 2014/0171863 A1 | | 6/2014 | Blacker | |

* cited by examiner

*Primary Examiner* — Emily Schmidt
*Assistant Examiner* — Lauren M Peng
(74) *Attorney, Agent, or Firm* — Rathe Lindenbaum LLP

(57) ABSTRACT

A robotic catheter system including a first drive mechanism configured to interact with an elongated medical device to cause the elongated medical device to move along its longitudinal axis. A wiper assembly includes a first wiping surface moving toward and away from the longitudinal axis. A controller provides a signal to a motor to move the first wiping surface toward the longitudinal axis when the elongated device is being withdrawn from a patient.

9 Claims, 2 Drawing Sheets

US 9,789,285 B1

WIPING MECHANISM FOR A Y-CONNECTOR

CROSS-REFERENCE TO RELATED PATENT APPLICATIONS

This application claims priority to U.S. Provisional Application No. 61/792,353 entitled Wiping Mechanism For A Y-Connector filed Mar. 15, 2013 and incorporated herein by reference in its entirety.

BACKGROUND

Guide wires are used to facilitate percutaneous procedures in which the guide wire is threaded into a human patient using X-ray guidance. The guide wires are manually threaded by a physician or other medical personnel but this requires that the operator be adjacent to the patient and so be in the immediate vicinity of the X-ray radiation providing the image used for guidance. Systems have been developed, such as that disclosed in U.S. Pat. No. 7,887,549 incorporated herein by reference, which allow the guide wires to be threaded into the patient robotically and thus allow the user or operator to be remote from the patient and the X-ray radiation. When the guide wire has been threaded into a blood vessel of a human patient it may be become contaminated with blood and if it is threaded into some other type of vessel it may become contaminated with some other bodily fluid. In the course of a procedure involving a guide wire it may become useful or necessary to withdraw it through the Y-connector and/or hemostasis valve.

SUMMARY

In one embodiment a robotic catheter system including a first drive mechanism configured to interact with an elongated medical device to cause the elongated medical device to move along its longitudinal axis. A wiper assembly includes a first wiping surface moving toward and away from the longitudinal axis. A controller provides a signal to a motor to move the first wiping surface toward the longitudinal axis when the elongated device is being withdrawn from a patient In another embodiment a wiping mechanism associated with a Y-connector and/or hemostasis valve wipes any bodily fluids which have become attached to the surface of a guide wire during its passage into a human patient as the guide wire is retracted before it enters or exits the Y-connector and/or hemostasis valve.

In a further embodiment, a method of cleaning an elongated medical device includes providing a first drive mechanism configured to interact with an elongated medical device to cause the elongated medical device to move along its longitudinal axis. A wiper assembly is provided having a first wiping surface moving toward and away from the longitudinal axis. The method further includes providing a control signal to a motor from a remote controller to move the first wiping surface toward the longitudinal axis of the elongated device when the elongated device is being withdrawn from a patient. The method also includes wiping fluid from an outer surface of the elongated medical device as the elongated medical device is begin withdrawn from the patient.

DETAILED DESCRIPTION

Figure 1:
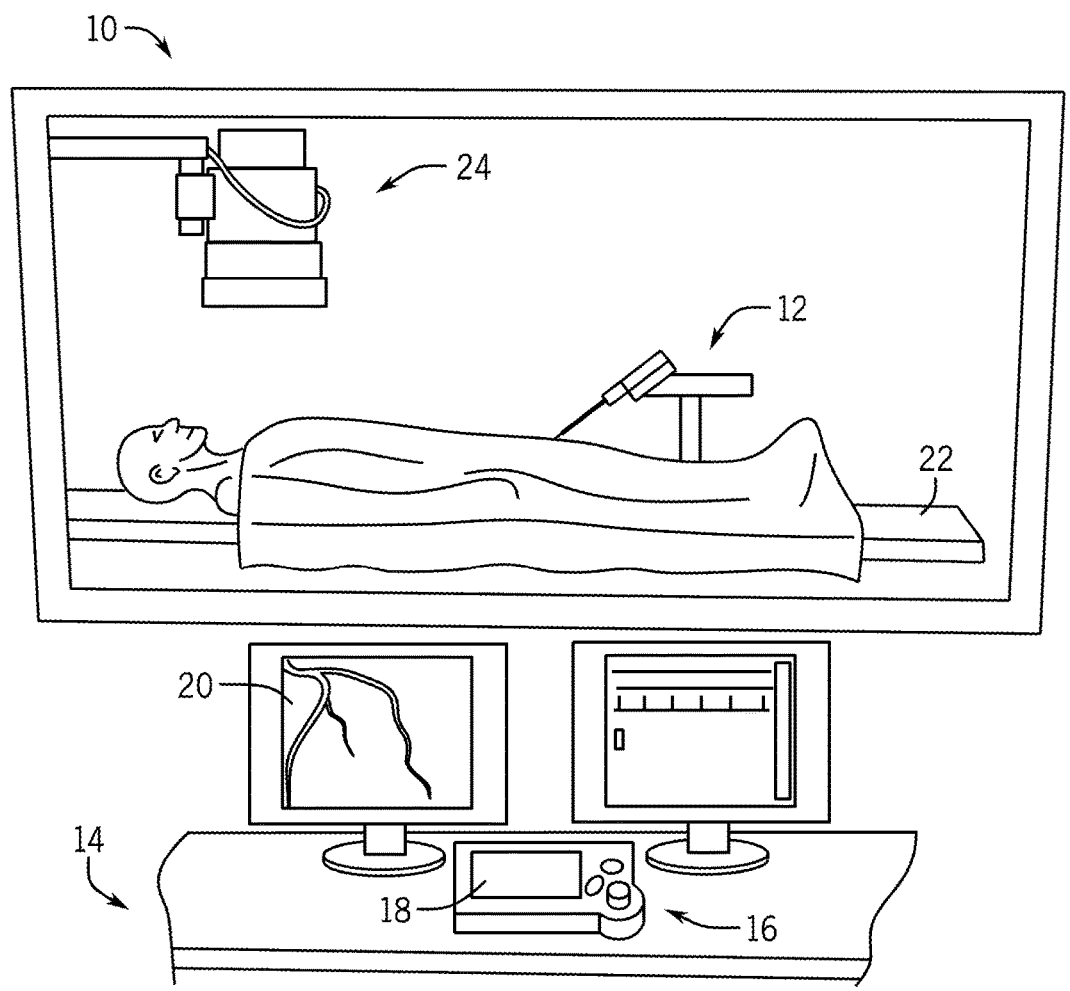
FIG. 1 is a schematic view of a wiper system proximate a hemostasis valve.

Referring to FIG. 1 a robotic system for manipulating an elongated medical device includes a bed side station 12 proximate a bed 22. A remote control station 14 includes a controller 16 having a user input 18 to control the bed side station 12. An x-ray source 24 is used in a Fluoroscopy system to provide an image on a display 20 in remote station 14. A robotic system such as that described in U.S. Pat. No. 7,887,549 may be used in conjunction with the wiper mechanism described herein.

Figure 2:
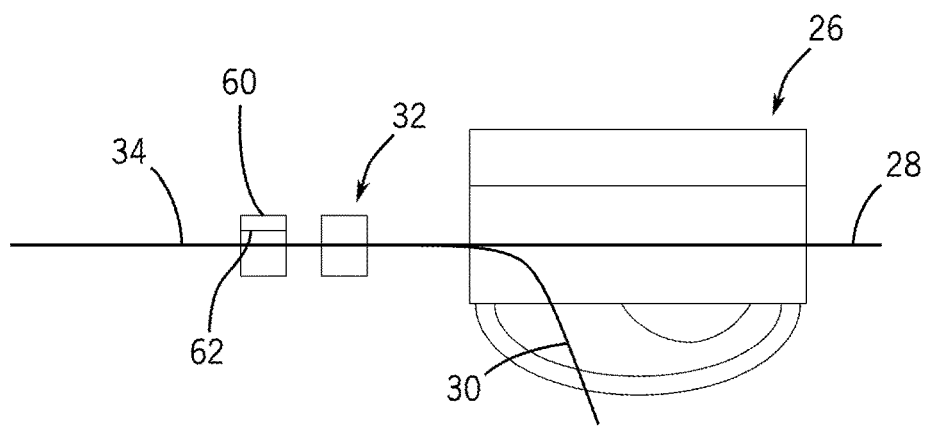
FIG. 2 to a top plan view a wiper system proximate a channel for an elongate medical device.
Figure 3:
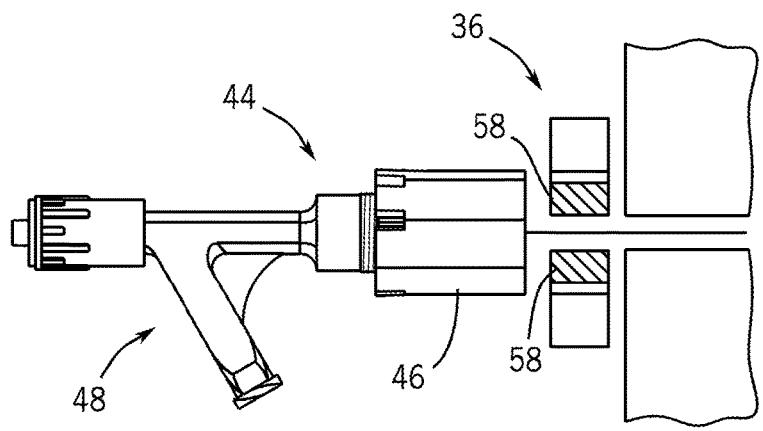
FIG. 3 is top view of a wiper mechanism at a distal portion of a cassette.

Referring to FIG. 2 a wiping mechanism or wiping assembly 32 may be positioned between a cassette 26 that is part of operatively connected to bed side station 12 and Y-connector and/or hemostasis valve and guide catheter 32. A guide wire 28 and/or working catheter may be subject to wiping mechanism 32 is deployed between the human patient and the Y-connect such that it contacts the surface of the guide wire or working catheter as it is retracted from a patient and before it interacts with the drive mechanisms of the cassette 26.

Figure 4:
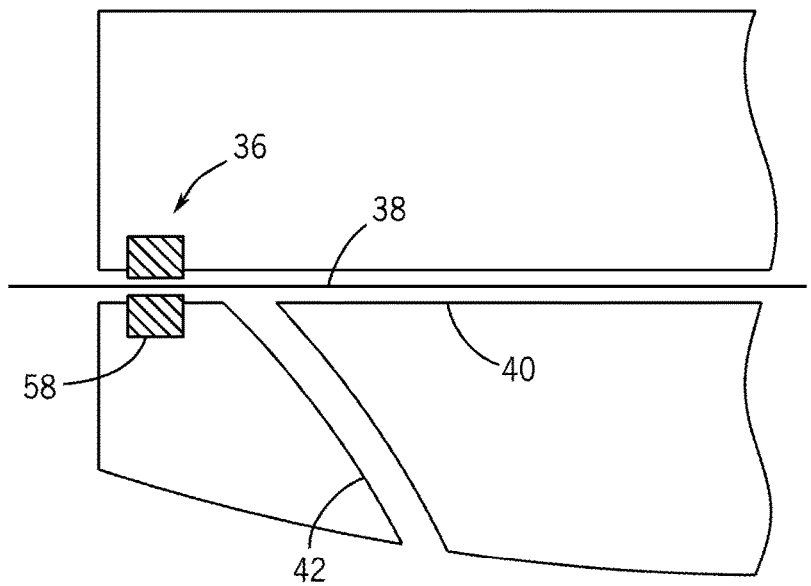
FIG. 4 is a view of the wiper mechanism intermediate a cassette and a Y-connector and hemostasis valve.

Referring to FIG. 4 a wiping mechanism assembly 36 is positioned between the cassette 26 and the Y-connector and/or hemostasis valve assembly 44. The assembly 44 includes a Y-connector 48 having at least two legs with each having a lumen in fluid communication with one another. A hemostasis valve 46 is operatively connected to one of the legs of the Y-connector 48.

Figure 5:
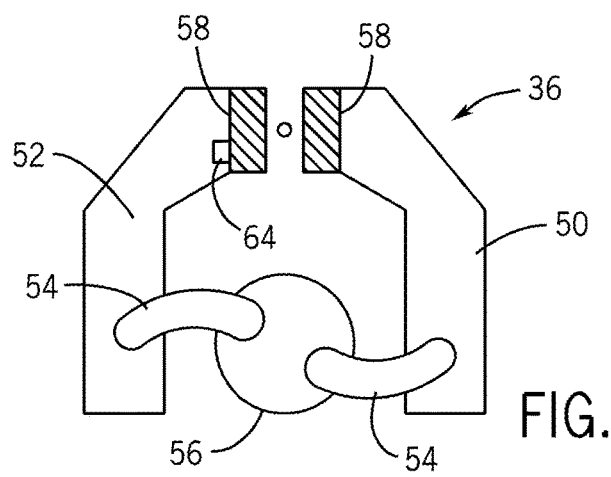
FIG. 5 is a cross sectional view of the wiper mechanism of FIG. 4.

Referring to FIG. 5 wiper assembly includes a resilient material 58 configured to wipe the outer surface of a guide wire being retracted from a patient into cassette 26 with a drive mechanism. Resilient material may be absorbent and act to wick and or wipe away fluid from the guide wire and/or working catheter as each is being withdrawn from the patient. Resilient material maybe mounted to two separate pads that are respectively attached to a first arm 50 and a second arm 52.

Arms 50 and 52 are operatively connected through linkages 54 that may be secured to a gear to drive 56. In this manner rotation of drive 56 causes the resilient opposing materials 58 to move toward and/or away from one another. The resilient pads may be robotically moved away from one another as the guide wire and/or working catheter are inserted into a patient to minimize friction to the guide wire and/or working catheter as these elongated medical devices are being inserted into a patient. The resilient pads may be robotically moved away from one another as the guide wire and/or working catheter is being withdrawn from a patient and withdrawn through the Y-connector and/or hemostasis valve.

In one embodiment the wiping mechanism involves two v-shaped members of a resilient material. In one embodiment these resilient members are connected to a mechanism which holds them out of contact with the guide wire when it is being fed forward into the human patient but which brings them into contact with the guide wire when it is being retracted into the Y-connector and/or hemostasis valve. In one embodiment these members are constructed of or carry an absorbent material such as natural or synthetic sponge such that they can absorb the bodily fluid which they wipe from the surface of the guide wire. In another embodiment an absorbent material is placed beneath or around these wiping members to absorb the bodily fluid which is wiped from the surface of the guide wire. In a further embodiment an aspiration apparatus is provided which aspirates the bodily fluid as it is wiped from the guide wire surface.

Figure 6:
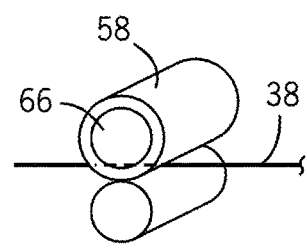
FIG. 6 is an isometric view of a roller wheel that rotates about an axis perpendicular to a longitudinal axis of an elongated medical device.

In another embodiment air may be blown over the guide wire proximate the resilient by an air curtain. In one embodiment a wiping fluid is provided by nozzles directed at the guide wire and activated when it is retracted to clean the guide wire. In this embodiment absorbent material may be provided beneath or around the guide wire to absorb the bodily fluid wiped from the guide wire by the stream of directed fluid. In another embodiment the directed fluid is air and/or a liquid and/or spray and the bodily fluid which it wipes from the guide wire is aspirated by a suction mechanism placed in the vicinity of the location on the guide wire where the air stream impinges on the wire. In a further embodiment, resilient material is attached to or part of roller wheels that rotates about an axis that is perpendicular to the longitudinal axis of the guide wire and/or working catheter. The rotation of the roller wheels minimizes the friction of the resilient wiping material with respect to the guide wire and/or working catheter. In one embodiment the wheel is driven by a motor when the elongated medical device is being withdrawn. In one embodiment the robotic catheter system includes a cleaner 60 depositing a fluid 62 on to the elongated medical device as the medical device is being withdrawn from the patient. In one embodiment the fluid is deposited by a remote controlled dispenser 60 and the rate of fluid flow is determined by the controller and a function of one or more of a user input, speed in which the elongated medical device is being withdrawn. In one embodiment a sensor 64 is configured to sense moisture on the wiping surfaces, the sensor providing a signal to a display on a remote station to alert a user that the wiping surface is saturated. In one embodiment the controller 16 automatically provides a signal to a motor to move a wiping surface away from the elongated medical device when the drive mechanism is driving the elongated medical device into a patient. Referring to FIG. 6 a roller wheel 66 rotates about an axis perpendicular to the longitudinal axis of the elongated medical device.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. Any of the features, elements, or components of any of the exemplary embodiments discussed above may be used alone or in combination with any of the features, elements, or components of any of the other embodiments discussed above. It is to be understood that the forms of the invention shown and described herein are to be taken as presently preferred embodiments. Elements and materials may be substituted for those illustrated and described herein, parts and processes may be reversed, and certain features of the invention may be utilized independently, all as would be apparent to one skilled in the art having the benefit of this description of the invention. Changes may be made in the elements described herein without departing form the spirit and scope of the invention as described in the following claims.

What is claimed is:

1. A robotic catheter system, the system comprising:
   a first drive mechanism configured to interact with an elongated medical device to cause the elongated medical device to move along its longitudinal axis;
   a wiper assembly having a first wiping surface moving toward and away from the longitudinal axis;
   a controller providing a signal to a motor to move the first wiping surface toward the longitudinal axis when the elongated medical device is being withdrawn from a patient; and
   a Y-connector and a hemostasis valve, the wiping surface being positioned intermediate the Y-connector and hemostasis valve and the first drive mechanism;
   wherein the first wiping surface contacts a surface of the elongated medical device to remove fluid from the elongated medical device;
   wherein the first wiping surface is on an exterior of a roller wheel that rotates about an axis that is perpendicular to the longitudinal axis of the elongated medical device.

2. The robotic catheter system of claim 1, wherein the first wiping surface is an absorbent material.

3. The robotic catheter system of claim 1, wherein the controller automatically provides a signal to a motor to move the first wiping surface away from the elongated medical device when the drive mechanism is driving the elongated medical device into a patient.

4. The robotic catheter system of claim 1, further including a cleaner depositing fluid on to the elongated medical device as the medical device is being withdrawn from the patient.

5. The robotic catheter system of claim 1, wherein the elongated medical device is a flexible guide wire.

6. The robotic catheter system of claim 1, wherein the wheel is driven by a motor when the elongated medical device is being withdrawn from the patient.

7. A robotic catheter system, the system comprising:
   a first drive mechanism configured to interact with an elongated medical device to cause the elongated medical device to move along its longitudinal axis;
   a wiper assembly having a first wiping surface moving toward and away from the longitudinal axis;
   a controller providing a signal to a motor to move the first wiping surface toward the longitudinal axis when the elongated medical device is being withdrawn from a patient; and
   a cleaner depositing a fluid on to the elongated medical device as the medical device is being withdrawn from the patient;
   wherein the first wiping surface contacts a surface of the elongated medical device to remove fluid from the elongated medical device;
   wherein the fluid is deposited by a remote controlled dispenser and the rate of fluid flow is determined by the controller and a function of one or more of a user input, speed in which the elongated medical device is being withdrawn.

8. A robotic catheter system, the system comprising:
   a first drive mechanism configured to interact with an elongated medical device to cause the elongated medical device to move along its longitudinal axis;
   a wiper assembly having a first wiping surface moving toward and away from the longitudinal axis, the wiper assembly includes a first arm supporting the first wiping surface, a second arm supporting a second wiping surface, and a linkage operatively connected to the motor and moving the arms toward and away from one another to move the first wiping surface and the second wiping surface toward and away from one another; and a sensor configured to sense moisture on the first wiping surfaces surface, the sensor providing a signal to a display on a remote station to alert a user that the first wiping surface is saturated.

9. A robotic catheter system, the system comprising:

a first drive mechanism configured to interact with an elongated medical device to cause the elongated medical device to move along its longitudinal axis;

a wiper assembly having a first wiping surface moving toward and away from the longitudinal axis; and a controller providing a signal to a motor to move the first wiping surface toward the longitudinal axis when the elongated medical device is being withdrawn from a patient;

wherein the first wiping surface contacts a surface of the elongated medical device to remove fluid from the elongated medical device;

wherein the wiper assembly includes a first arm supporting the first wiping surface, a second arm supporting a second wiping surface, and a linkage operatively connected to the motor and moving the arms toward and away from one another to move the first wiping surface and the second wiping surface toward and away from one another.

\* \* \* \* \*